(12) United States Patent
He et al.

(10) Patent No.: US 7,127,298 B1
(45) Date of Patent: Oct. 24, 2006

(54) SWITCHED-MATRIX OUTPUT FOR MULTI-CHANNEL IMPLANTABLE STIMULATOR

(75) Inventors: Yuping He, Northridge, CA (US); David K. L. Peterson, Saugus, CA (US); Jordi Parramon, Valencia, CA (US)

(73) Assignee: Advanced Bionics Corporation, Sylmar, CA (US)

( * ) Notice: Subject to any disclaimer, the term of this patent is extended or adjusted under 35 U.S.C. 154(b) by 553 days.

(21) Appl. No.: 10/686,219

(22) Filed: Oct. 15, 2003

Related U.S. Application Data

(60) Provisional application No. 60/419,684, filed on Oct. 18, 2002.

(51) Int. Cl.
*A61N 1/08* (2006.01)
(52) U.S. Cl. .............................. 607/48; 607/2; 607/57; 607/117
(58) Field of Classification Search .................. 607/9, 607/43, 48, 57, 117
See application file for complete search history.

(56) References Cited

U.S. PATENT DOCUMENTS

| | | |
|---|---|---|
| 3,646,940 A | 3/1972 | Timm et al. |
| 3,724,467 A | 4/1973 | Avery et al. |
| 3,822,708 A | 7/1974 | Zilber |
| 4,254,776 A * | 3/1981 | Tanie et al. .................. 607/63 |
| 4,532,930 A | 8/1985 | Crosby et al. |
| 4,592,359 A | 6/1986 | Galbraith |
| 4,726,379 A * | 2/1988 | Altman et al. ................ 607/9 |
| 4,947,844 A | 8/1990 | McDermott |
| 5,776,172 A | 7/1998 | Schulman et al. |
| 6,002,966 A * | 12/1999 | Loeb et al. .................. 607/57 |
| 6,067,474 A | 5/2000 | Schulman et al. |
| 6,181,969 B1 | 1/2001 | Gord |
| 6,381,496 B1 | 4/2002 | Meadows et al. |
| 6,516,227 B1 | 2/2003 | Meadows et al. |
| 6,622,048 B1 | 9/2003 | Mann et al. |
| 2003/0114899 A1 | 6/2003 | Woods et al. |
| 2003/0120323 A1 | 6/2003 | Meadows et al. |

FOREIGN PATENT DOCUMENTS

WO    WO-02/09808 A1    2/2002

* cited by examiner

*Primary Examiner*—Robert E. Pezzuto
*Assistant Examiner*—Brian T. Gedeon
(74) *Attorney, Agent, or Firm*—Vista IP Law Group LLP

(57) ABSTRACT

The invention is a switched-matrix output for a multi-channel stimulator. The switch-matrix output system uses groups of switches connectively placed between N number of digital-to-analog convertors (DACs) and M electrode contacts to permit fewer, space-consuming DACs to be used in an implantable stimulator, thereby saving internal stimulator space. One embodiment of the switched matrix output uses switches to activate only one active-electrode subset of M electrode contacts at any one time, so that the total number of DACs contained in the stimulator can be less than the M total number of electrode contacts.

19 Claims, 6 Drawing Sheets

SWITCHED-MATRIX OUTPUT FOR MULTI-CHANNEL IMPLANTABLE STIMULATOR

The present application claims the benefit of U.S. Provisional Application Ser. No. 60/419,684, filed 18 Oct. 2002, which application is herein incorporated by reference in its entirety.

BACKGROUND OF THE INVENTION

The present invention relates to implantable stimulators and, specifically, methods and systems for delivering stimulation through multiple output channels.

Multi-channel stimulators are used in a number of implantable medical devices. For example, a cochlear device for restoration of hearing is an exemplary device which uses a multi-channel stimulator. Representative prior art cochlear implant systems are disclosed in U.S. Pat. Nos. 4,592,359; 4,947,844; 5,776,172; and 6,067,474, all of which are herein incorporated by reference. Another use of implantable, multi-channel stimulators include those for spinal cord stimulation for treating intractable pain. Representative spinal cord stimulation (and electrode) systems are disclosed in International Publication Number WO 02/09808 A1 and in U.S. Pat. Nos. 3,646,940; 3,724,467; and 3,822,708, all of which are herein incorporated by reference.

Such multi-channel, implantable stimulators presently have the capability of driving up to 16 electrodes and have increased processing capability. The large number of channels and advanced processing capability typically consume more power than devices having fewer channels. The long-term trend is toward using more channels while more processing capability is added. In cochlear applications, more channels can be used to provide higher resolution of perceived sounds. For spinal cord stimulation, having more channels affords greater flexibility in shaping current stimulation fields after the lead is implanted so that the initial lead placement is less critical for successfully inducing paresthesia to overlap the regions of pain.

While enhanced processing is desired, a concurrent goal is to decrease the size of the implanted device while making the battery last longer. Making the device smaller is advantageous for a number of reasons. One reason is that implantation can be less invasive and, hence, less susceptible to infection. Another reason is that the device is less obtrusive once implanted under the skin, within the skull, or within the body.

Thus, it is evident that there is a need for systems and methods of reducing the space taken up by circuitry in an implantable stimulator. The space thus saved can be used to reduce the overall size of the implanted device or, alternatively, used to implant a larger battery in the saved space to enable more channels, more processing power or longer device life.

SUMMARY OF THE INVENTION

The present invention addresses the above and other needs by overcoming the disadvantages enumerated above by providing systems and methods for switching the stimulation outputs (electrode contacts) to conserve critical space inside an implantable stimulator.

In accordance with one aspect of the invention, there is provided a system for implementing a switched-matrix output for a multi-channel stimulator. The stimulation output system comprises: N number of DACs; M number of electrode contacts; and a total of N×M switches. Each of N number of DACs is coupled to one group of switches (consisting of M number of switches). Each switch within one group of switches, in turn, is coupled to one of M electrode contacts. M is greater than N, and M and N are whole numbers.

In another embodiment of the present invention, the system comprises: N number of DACs; M number of electrode contacts; L active electrode contact groups; and M total number of switches. There is N number of electrode contacts in one active electrode group and each of N number of DACs is coupled to one of the N grouped set of switches, each grouped set of switches comprising 1 to L switches. Each switch in the one of N set of switches, in turn, is uniquely coupled to only one electrode contact in each of 1 to L active electrode groups. The whole numbers N, L and M are chosen such that N×L=M, and wherein M is greater than N.

In another aspect of the invention a method of switching output is provided, the method comprising: providing N number of DACs; providing M number of electrode contacts; coupling each of N number of DACs to M switches; coupling each of the M switches uniquely to each of M electrode contacts; and connecting selected switches by closing these switches which thereby connects the selected electrode contacts to transmit current, while at the same time, avoiding closing more than one switch that permits connecting the same electrode contact to more than a single DAC or current source. M and N are whole numbers and M is greater than N and there is at least N×M total number of switches.

In yet another embodiment of the method of switching output in a multi-channel stimulator, the method comprises: providing N number of DACs; providing M number of electrode contacts and M number of switches; coupling each of N number of DACs to at least one set of switches having L number of switches; coupling each switch within the at least one set of switches uniquely to one of the M electrode contacts; and causing current to flow through selected electrode contacts (usually an activated group of electrodes) at any one time duration $T_d$ by closing the associated switches. The whole numbers N, L and M are chosen such that M=N×L, and M is greater than N. Groups of electrode contacts may thereby be activated in a time-multiplexed sequence.

It is thus a feature of the present invention to provide a switching system and method which permits use of fewer DACs then electrode contacts, thereby saving limited device space.

It is a further feature of the invention to take advantage of the fact that not all electrode contacts are stimulated (active) at any one time, and thus, switches may be used to activate those active electrode groups which are "on" at any one time.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1A:
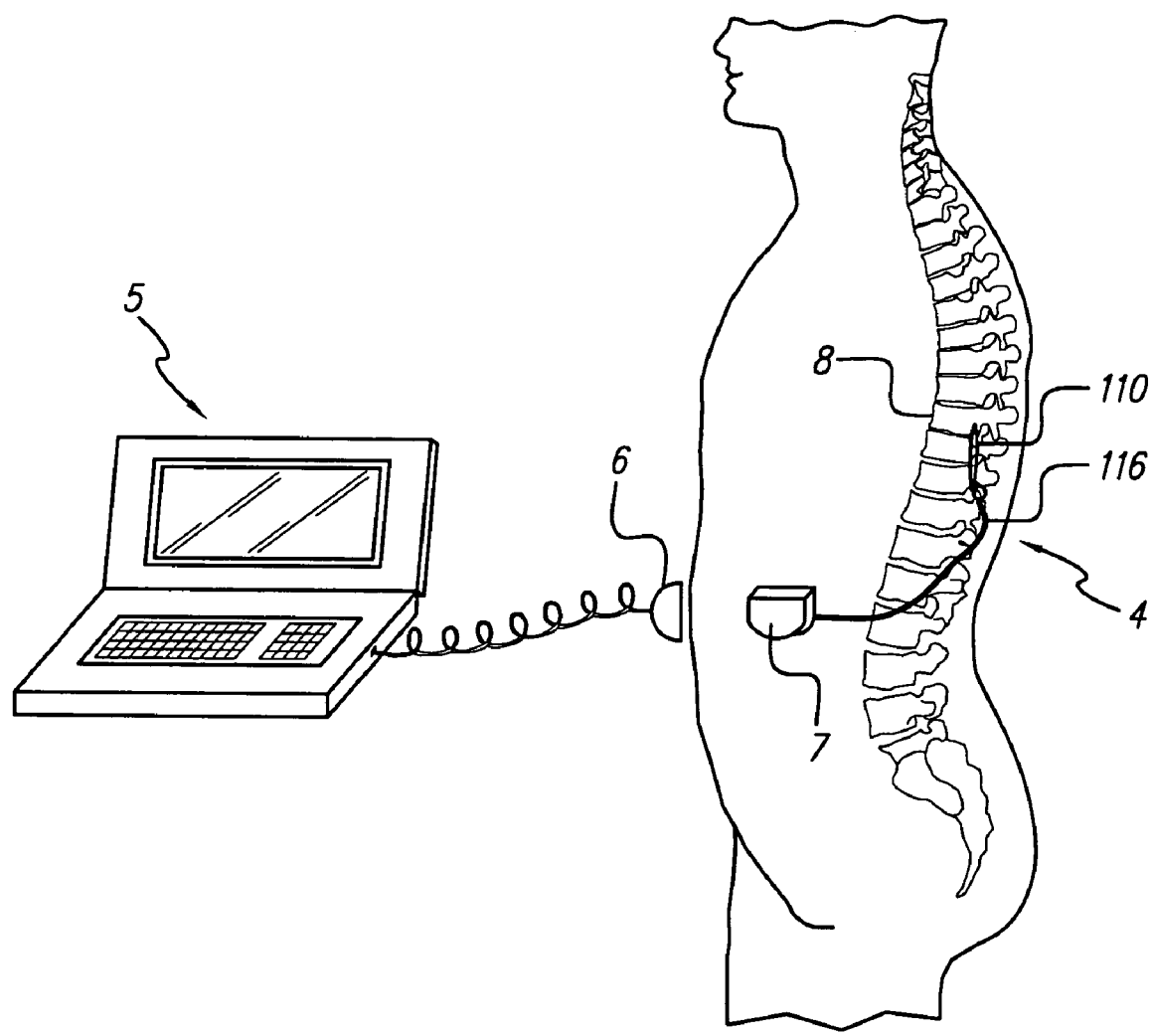
FIG. 1A shows a cut-away, vertical view of a patient with a spinal cord stimulator implanted.

FIG. 1A shows a side, cut-away view of a patient 4 and a generalized, implantable, spinal cord stimulation system. The implantable system includes an IPG 7 and lead 116 connected to an electrode array 110. The IPG 7 contains electrical circuitry powered by an internal battery, which circuitry can output current pulses to each stimulation channel and through electrode contacts comprising the electrode array. Each stimulation channel can be connected to at least one electrode contact on the electrode array. The electrode contact provides current to the tissue to be stimulated. Communication with the IPG can be accomplished with an external programmer 5, using a programmer head 6.

Figure 1B:
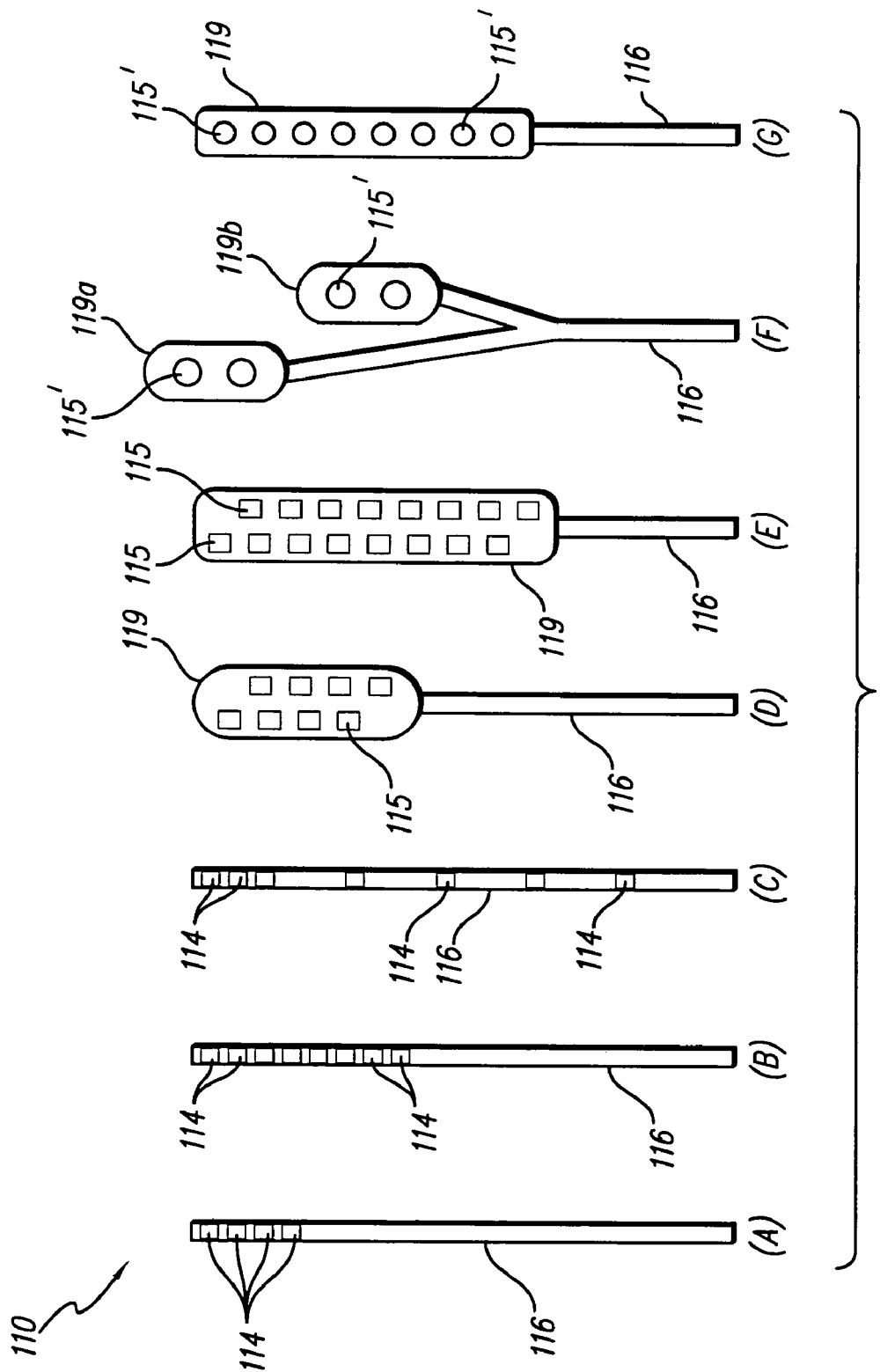
FIG. 1B illustrates various configurations of electrode arrays that may be used with a multi-channel stimulator.

FIG. 1B shows various embodiment of electrode arrays 110. Embodiments (A) through (C) show electrode arrays having in-line electrodes 114 placed on the lead 116. Embodiments (D), (E), (F) and (G) show various paddle-type electrode arrays on a paddle-shaped substrate 119, 119a, and 119b. The electrodes 115, 115' can be positioned in parallel columns, as depicted in illustrations (D) and (E), or on separate paddles as in (F), or in-line as in (G). These examples illustrate only a few possible configurations of electrode arrays 110 that may be used with a multi-channel stimulator having a multiplicity of outputs (electrode contacts).

Figure 2:
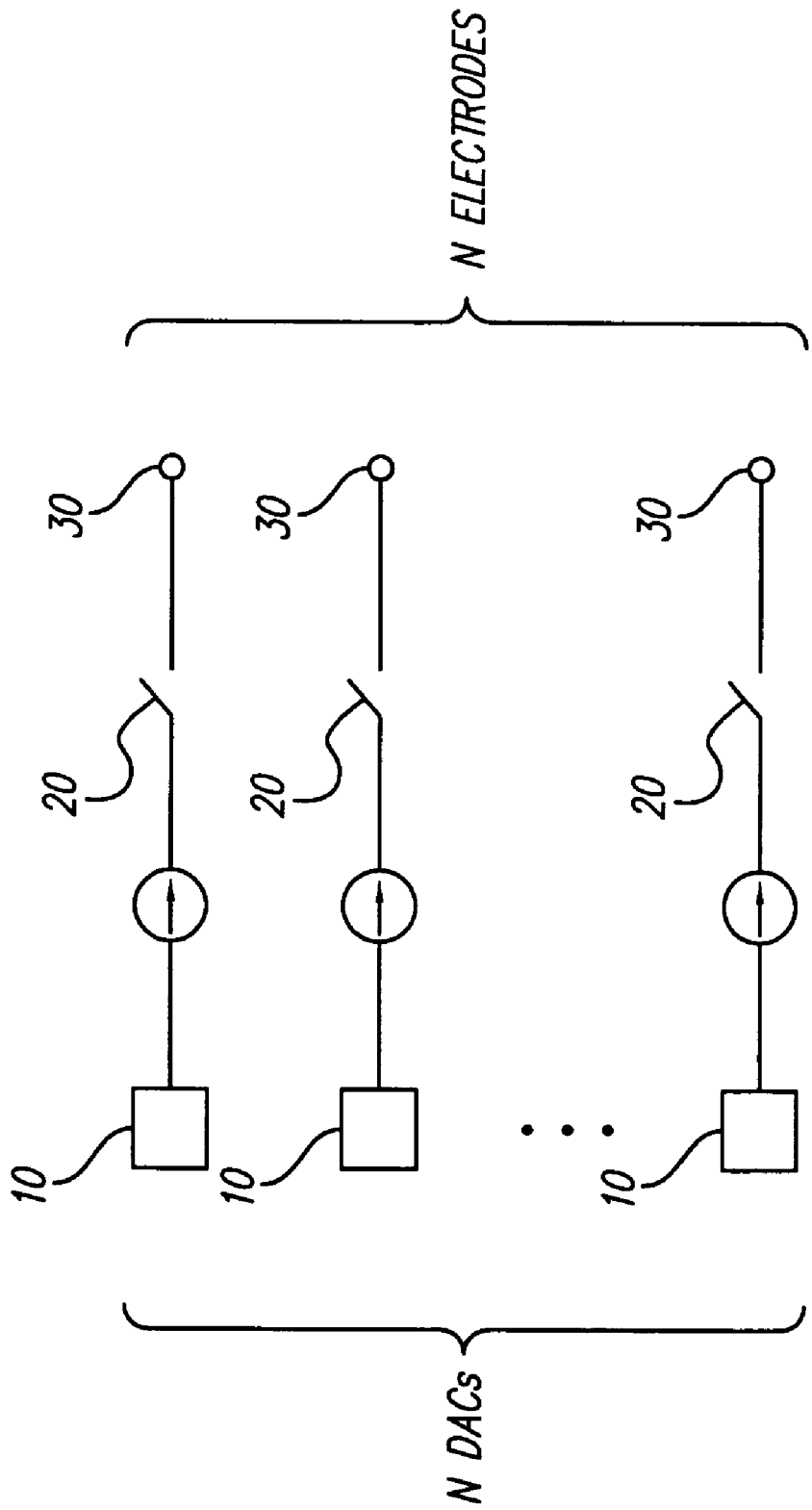
FIG. 2 shows a fragmentary circuit diagram of a presently practiced circuit in which N digital-to-analog converters (DACs) are uniquely linked to one of N stimulation outputs.

FIG. 2 shows a fragmentary circuit diagram of a presently practiced circuit in which N number of digital-to-analog converters (DACs) 10 are uniquely linked to one of N stimulation outputs (electrode contacts) 30. A switch 20 is used to activate and deactivate a connection between the DAC and stimulation output. The switching system shown can be practically used for multi-channel stimulators which have a small number of outputs (electrode contacts). For example, most commercially available spinal cord stimulators do not exceed four channels and so this conventional output connection scheme is workable. Some spinal cord stimulators may employ eight channels and thus a lead or leads having a total of sixteen electrode contacts can be used. For a sixteen channel, monopolar stimulation system, sixteen DACs would need to be used with the conventional output method. Bipolar stimulation systems can also be configured using P-DAC and N-DAC circuits as taught, e.g., in U.S. Pat. No. 6,181,969.

The trend in the field of implantable medical devices is to increase the total number of stimulation channels in order to gain increased stimulation flexibility. Because DACs occupy a high percentage of the space used by the analog circuitry in multi-channel stimulators, it can be appreciated that increasing the number of stimulation channels will undesirably increase the number of DACs and, disadvantageously, require the use of additional space in the medical device. Such use of space is critical in an implantable device since it is desirable to keep the device size down while increasing the storage capacity of the battery used to power the device and increasing the processing capability of the device. By reducing the size of the circuitry, the device size may be reduced or, alternatively, the size of the battery may be increased. The present invention, as described below, enables more stimulation channels (and electrode contacts) to be added while reducing the use of spacing consuming DACs.

Figure 3:
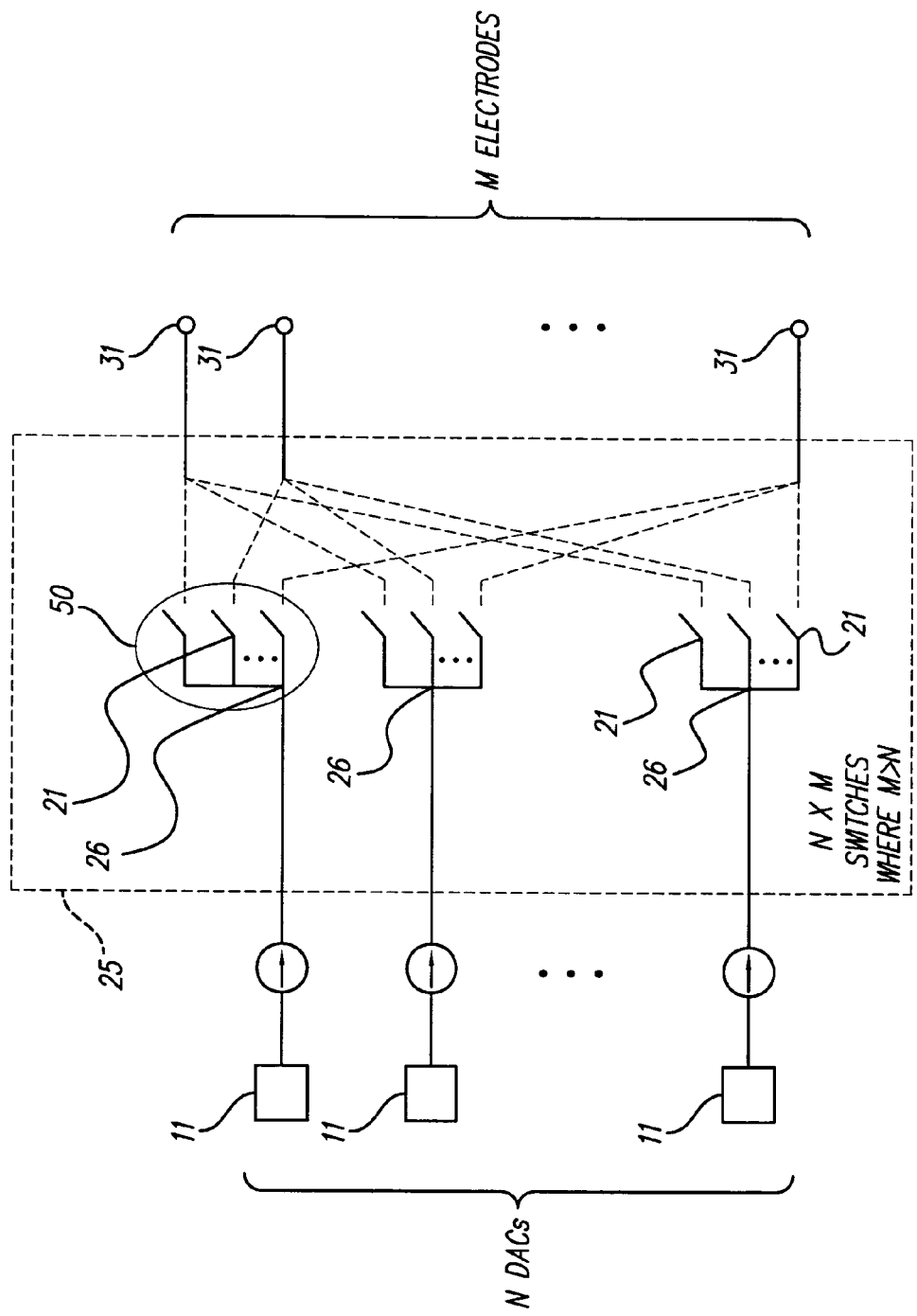
FIG. 3 shows a fragmentary circuit diagram, in accordance with the present invention, in which N×M total number of switches are used to connect N number of DACs to M stimulation outputs (electrode contacts)

FIG. 3 shows a fragmentary circuit diagram, in accordance with the present invention, in which N number of DACs 11 can be connected to M stimulation outputs (electrode contacts) 31 using N×M total number of switches 21. The N×M switches 21 may be part of an integrated switching module 25. It can be seen that each DAC 11 is coupled uniquely to a node 26 which, in turn, is connected to a group 50 of M number of switches 21. Each switch 21 can further be connected to each one of the M number of single outputs (an electrode contact) 31. While each switch 21 can only be coupled to one electrode contact 31 by closing the switch 21, each electrode contact 31, however, may potentially be switched to N number of possible switches 21.

The switches 21 may be transistors configured as switches and may include PMOS or MOS transistors. The switches 21 may be controlled and programmed by a software program or through hardware implementation to prevent connection of two sources of current, i.e., two NDACs 11, to a single electrode contact 31.

N, the number of DACs employed is less than M, the total number of outputs or electrode contacts 31. This represents a reduction in the number of total DACs as compared to the conventional design of FIG. 2, where the number of DACs equals the number of outputs (electrode contacts).

In operation, the electrode contacts may be selectively switched using the method of the present invention, the method comprising: (a) providing N number of DACs (11); (b) providing M number of electrode contacts (31); (c) coupling each of N DACs (11) to a group of M switches (31); (d) coupling each of the M switches (31) uniquely to each of M electrode contacts (31); and (e) connecting selected switches (21) by closing the switches, to electrically connect selected electrode contacts (31) to transmit current, while avoiding closing more than one switch (21) connected to the same electrode contact (31) at any one time.

Each of the N number of DACs may provide a current that is a different or same amplitude. Not all the DACs need to be operating at the same time. It is also possible that the DACs are all operating at the same time, but the switches, which may be programmed, can be closed to permit current to flow through only selected electrode contacts 31. It is important that current does not flow from more than a single source, e.g., a DAC, to an electrode contact 31 at any one time.

It can also be seen that it may be possible to activate two separate electrode contacts 31 using the same DAC 11 by closing two switches 21 within the same group 50 of M switches. Thus, while there are only N number of DACs, which is less than M, the number of electrode contacts, it may be possible to activate every electrode contact 31 at one time, although some of the electrode contacts may have the same level of current flowing as they derive from the same DAC.

Figure 4A:
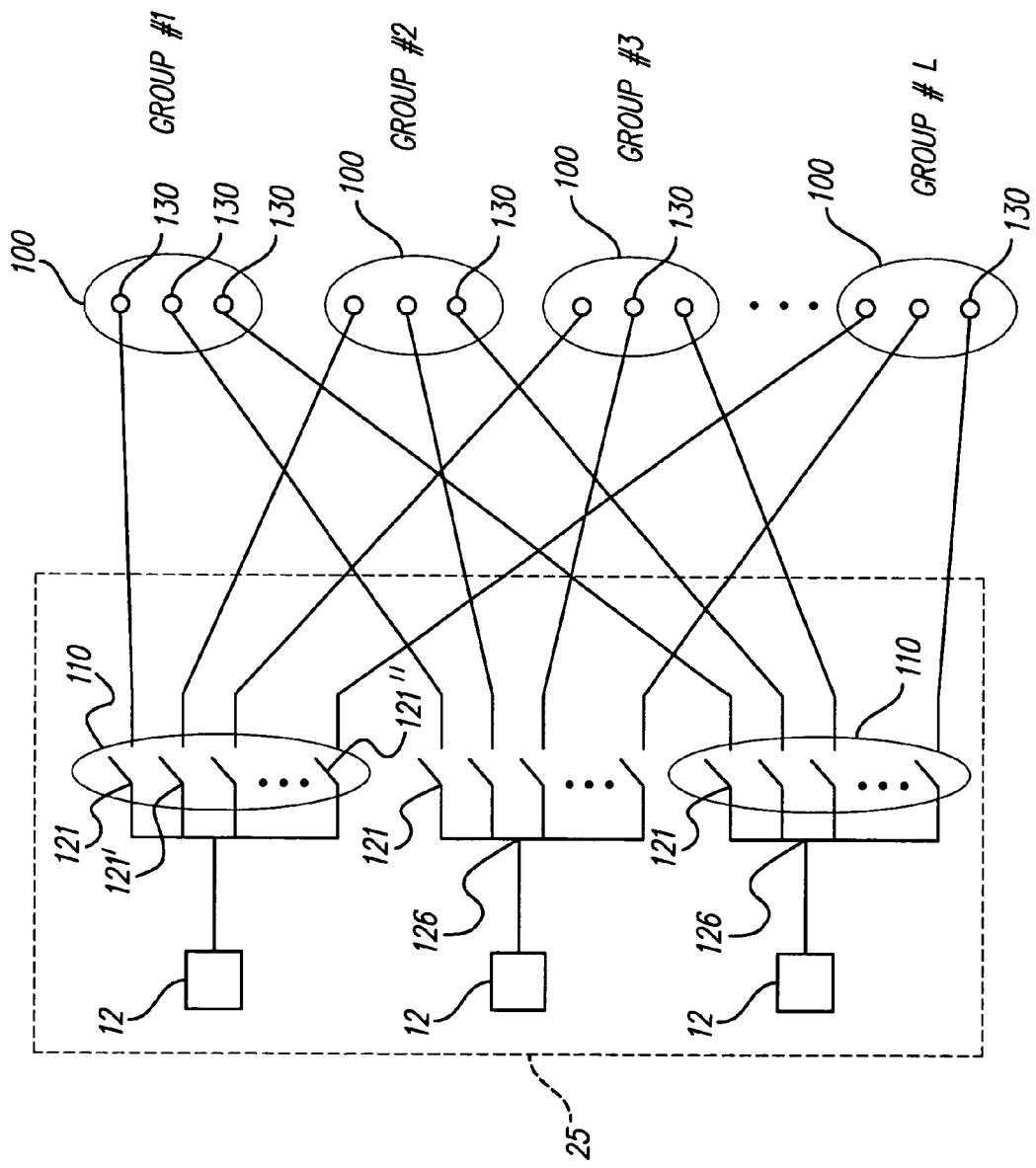
FIG. 4A shows a fragmentary circuit diagram, in accordance with the present invention, in which M total number of switches are used to connect N number of DACs to M stimulation outputs (electrode contacts)

FIG. 4A shows a fragmentary circuit diagram, in accordance with another embodiment of the present invention. The system shown in FIG. 4A takes advantage of the fact that, in many multi-channel stimulators, not all stimulation channels are active (turned on) at any given moment. Only one group of electrodes 100 may be active (the "active electrode group") at any one time duration, $T_d$. Each active electrode group is labeled #1 through #L in FIG. 4A. L also signifies the number of switches 121 in one set or group 110 of switches 121, connected to one DAC 12. Each active electrode group 100 includes N number of outputs (electrode contacts) 130. In addition N signifies the number of available DACs 12. There is a total of M number of switches 121 each uniquely coupled to M number of outputs (electrode contacts) 130.

The parameters are related as follows: M (number of electrodes)=M (total number of switches)=N (number of DACs)×L (number of switches in one set of switches)=L (number of active electrode groups)×N (number of electrodes in one active electrode group). M and N are whole number and M is greater than N.

The switching matrix in FIG. 4A is configured so that one DAC 12 is uniquely coupled to one grouped set 110 of L number of switches 121. Each DAC 12 is connected to a node 126 which, in turn, is connected to one grouped set of 110 of L number of switches 121. Each switch 121 uniquely connects to only one electrode contact 130. Also, each active group 110, numbered 1 through L draws only one connection from each set 110 of grouped switches. For instance, in the first set of switches 110, first switch 121 connects to one electrode in active electrode group #1, the second switch 121' connects to one electrode in active electrode group #2 and so on, until the last switch 121" is connected to one electrode in active electrode group #L. The M number of total switches 121 may be part of an integrated switching module 25.

In operation, the outputs (electrode contacts) may be switched in a multi-channel stimulator, in accordance with the following method which comprises: (a) providing N number of DACs (12); (b) providing M number of electrode contacts (130) and M number of switches (110); (c) coupling each of N DACs (12) to at least one set (110) of switches having L number of switches (121) in the at least one set (110); (d) coupling each switch (121) within the at least one set (110) of switches, uniquely to one of the M electrode contacts (130); and (e) causing current to flow through selected electrode contacts (130) at any one time duration, $T_d$, by closing the associated switches (121).

Each of the N number of DACs may provide a current that is a different or the same amplitude. Not all the DACs need to be operating at the same time. It is also possible that the DACs are all operating but the switches, which may be programmed, can be closed to permit current to flow through only selected electrode contacts 130.

It can also be seen that it may be possible to activate two separate electrode contacts 130 using the same DAC 12 by closing two switches 121 in the same group 110 of M switches. Thus, while there are only N number of DACs, which is less than M, the number of electrode contacts, it may be possible to activate every electrode contact 130 at one time, although some of the electrode contacts may have the same level of current flowing as they derive from the same DAC. In general, however, groups 100 of electrode contacts, e.g., Group #1 in a first time interval, Group #2 in a second time interval and Group #3 in a third time interval and so on will be activated in a time-multiplexed manner, permitting current to flow through the selected groups 100 of electrode contacts when activated.

Figure 4B:
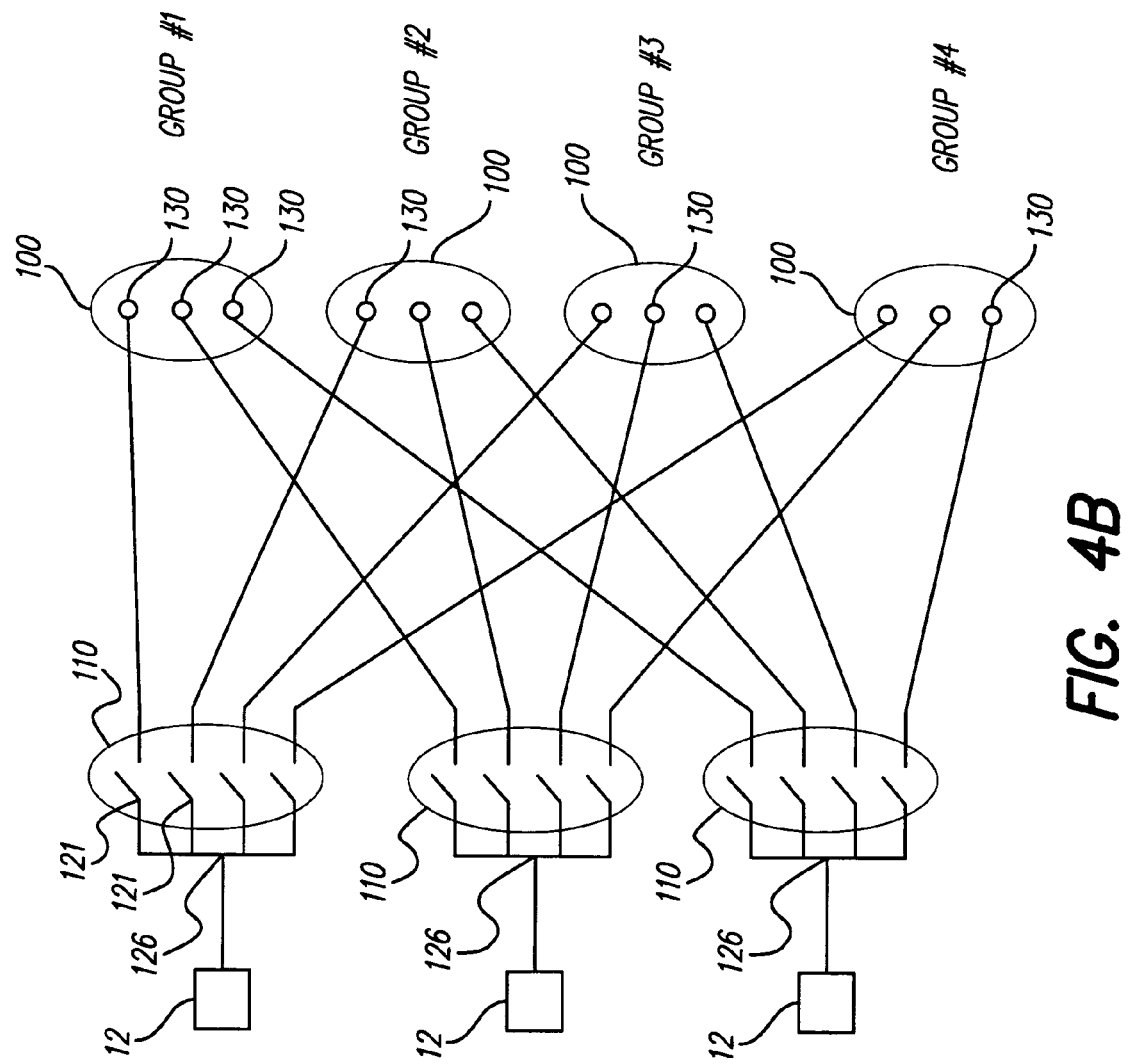
FIG. 4B shows a specific example of the embodiment of the switching matrix as depicted in FIG. 4A, wherein there are three DACs, twelve outputs (electrode contacts), and twelve switches.

FIG. 4B shows a specific example of the generalized system shown in FIG. 4A. The specific example shows an switching configuration in which M=12, L=4, and N=3. It can be seen in this example, that N (number of DACs)×L (switches in one set of switches)=N (electrodes in one active electrode group)×L (number of active electrode group)=M (number of electrodes or number of switches). This simple example illustrates that the electrode contacts in groups #1 through #L may be activated one group at a time, or alternatively, it may be possible to activate all the electrode contacts by closing all of the switches 121, although the current derived from a single DAC 12 would be divided up into many electrode contacts. Preferably, in order to transmit usable current levels, groups of electrode contacts are activated in a time multiplexed manner, e.g., Group #1 is activated (with all other Groups not activated), then Group #2 is activated (with all other Groups not activated), then Group #3 is activated (with all other groups not activated), and so on.

In summary, the present invention enables the use of fewer DACs and thereby saves precious device space by employing a switching matrix method and system. When only a subset of the electrodes are active at any one time, the switching matrix method and system of the present invention can further reduce the number of DACs needed in an implantable, multi-channel stimulator.

While the invention herein disclosed has been described by means of specific embodiments and applications thereof, numerous modifications and variations could be made thereto by those skilled in the art without departing from the scope of the invention set forth in the claims. Specifically, it will be appreciated by those skilled in the art that while the invention has been described with respect to incorporation into a multi-channel, spinal cord stimulator or a cochlear stimulator, the method and system described may be used equally in other multi-channel neural stimulators in which DACs are employed.

What is claimed is:

1. A stimulation output switching system for a multi-channel stimulator, said system comprising:
   N number of DACs (11);
   M number of electrode contacts (31); and
   N×M number of switches (21);
   wherein each DAC (11) of the N number of DACs is coupled uniquely to one group (50) of M number of switches (21), each switch within each group (50) of M switches, in turn, is coupled to each one of M electrode contacts (31); and
   wherein M and N are whole numbers and M is greater than N.

2. The system of claim 1 wherein the switches are transistor switches.

3. The system of claim 2 wherein the transistor switches are selected from the group consisting of PMOS or MOS transistors.

4. The system of claim 1 wherein the switches are programmable using software or hardware programming.

5. The system of claim 4, wherein the programming allows one and only one switch (21), at any one time, to be electrically closed (connected) to one particular electrode contact (31), and thereby permit current to flow through that single electrode contact.

6. A stimulation output switching system for a multi-channel stimulator, said system comprising:

N number of DACs (12);

M number of switches (121), grouped into N grouped sets (110) of switches, each set (110) having L number of switches (121);

M number of electrode contacts (130); and

L number of electrode contact groups (100), wherein each DAC (12) of the N number of DACs is coupled to one of the N grouped sets (110) of switches (121);

wherein each switch (121) in one of the N set (110) of switches, in turn, is uniquely coupled to only one electrode contact (130) in each of L groups (100) of electrode contacts;

wherein the whole numbers N, L and M are chosen such that, N×L=M; and wherein M is greater than N.

7. The system of claim 6 wherein the switches are transistor switches.

8. The system of claim 7 wherein the transistor switches are selected from the group consisting of PMOS or MOS transistors.

9. The system of claim 6 wherein the switches are programmable using software or hardware programming.

10. The system of claim 9 wherein the programming allows electrode contacts (130) only one electrode contact group (100) or, a subset thereof, among the L contact groups (100) to pass current in a single time duration $T_d$.

11. A method of switching outputs in a multi-channel stimulator, said method comprising:

(a) providing N number of DACs (11);

(b) providing M number of electrode contacts (31);

(c) coupling each of N DACs (11) to a group of M switches (31);

(d) coupling each of the M switches (31) uniquely to each of M electrode contacts (31); and (e) connecting selected switches (21) by closing the switches, to electrically connect selected electrode contacts (31) to transmit current, while avoiding closing more than one switch (21) connected to the same electrode contact (31) at any one time, wherein there is at least N×M total number of switches (31); and wherein M and N are whole numbers and M is greater than N.

12. The method of claim 11 wherein the switches are transistor switches.

13. The method of claim 12 wherein the transistor switches are selected from the group consisting of PMOS or MOS transistors.

14. The method of claim 11 wherein the step (e) of connecting switches is accomplished by using software or hardware programming.

15. A method of switching outputs in a multi-channel stimulator, said method comprising:

(a) providing N number of DACs (12);

(b) providing M number of electrode contacts (130) and M number of switches (110);

(c) coupling each of N DACs (12) to at least one set (110) of switches having L number of switches (121) in the at least one set (110);

(d) coupling each switch (121) within the at least one set (110) of switches, uniquely to one of the M electrode contacts (130); and (e) causing current to flow through selected electrode contacts (130) at any one time duration, $T_d$, by closing the associated switches (121), wherein the whole numbers N, L and M are chosen such that M=N×L, and M is greater than N.

16. The method of claim 15 wherein the switches are transistor switches.

17. The method of claim 16 wherein the transistor switches are selected from the group consisting of PMOS or MOS transistors.

18. The method of claim 15 wherein the switches are software programmable.

19. The method of claim 15 wherein the step (e) of causing current to flow through a selected group of electrode contacts is accomplished by causing current to flow in only one of L number of electrode contact groups (100) at any one time duration, $T_d$.

* * * * *